United States Patent
Sugerman

(10) Patent No.: US 9,168,280 B1
(45) Date of Patent: *Oct. 27, 2015

(54) BOTANICAL COMPOSITION AND METHOD FOR TREATING PAIN AND DISCOMFORT OF VARIOUS CONDITIONS

(71) Applicant: Seven Consulting, Inc., Arlington, VA (US)

(72) Inventor: Michael Sugerman, Alexandria, VA (US)

(73) Assignee: Kage Apothecare, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/689,767

(22) Filed: Apr. 17, 2015

Related U.S. Application Data

(63) Continuation of application No. 13/933,764, filed on Jul. 2, 2013, now Pat. No. 9,040,099, which is a continuation-in-part of application No. 13/834,018, filed on Mar. 15, 2013, which is a continuation-in-part of application No. 13/287,168, filed on Nov. 2, 2011, now Pat. No. 8,501,248.

(60) Provisional application No. 61/409,305, filed on Nov. 2, 2010.

(51) Int. Cl.
| | |
|---|---|
| A61K 36/00 | (2006.01) |
| A61K 36/9066 | (2006.01) |
| A61K 36/738 | (2006.01) |
| A61K 36/45 | (2006.01) |
| A61K 36/76 | (2006.01) |
| A61K 36/185 | (2006.01) |
| A61K 9/50 | (2006.01) |

(52) U.S. Cl.
CPC . *A61K 36/76* (2013.01); *A61K 9/50* (2013.01); *A61K 36/185* (2013.01); *A61K 36/738* (2013.01); *A61K 36/9066* (2013.01)

(58) Field of Classification Search
None
See application file for complete search history.

(56) References Cited

U.S. PATENT DOCUMENTS

| | | |
|---|---|---|
| 5,437,866 A | 8/1995 | Sun |
| 5,627,195 A | 5/1997 | Hu |
| 5,665,393 A | 9/1997 | Chen et al. |
| 5,683,697 A | 11/1997 | Tani |
| 6,541,045 B1 | 4/2003 | Charters et al. |
| 7,931,922 B2 | 4/2011 | Newmark et al. |
| 7,989,009 B2 | 8/2011 | Kandaswami et al. |
| 2004/0001817 A1 | 1/2004 | Giampapa |

OTHER PUBLICATIONS

Hussin et al, Protective effect of *Centella asiatica* extract and powder on oxidative stress in rats. Food Chemistry (2006), vol. Date 2007, 100(2), 535-541.
Farr et al, The antioxidants .alpha.-lipoic acid and N-acetylcysteine reverse memory impairment and brain oxidative stress in aged SAMP8 mice. Journal of Neurochemistry (2003), 84(5), 1173-1183.
Schmid et al, Benfotiamine exhibits direct antioxidative capacity and prevents induction of DNA damage in vitro. Diabetes/metabolism research and reviews, (Jul.-Aug. 2008) vol. 24, No. 5, pp. 371-377.
Vij et al, Inhibitory effect of seabuckthorn (*Hippophea rhamnoides*) on platelet aggregation and oxidative stress. Journal of Complementary and Integrative Medicine, (2010) vol. 7, No. 1. arn. 7.

*Primary Examiner* — Qiuwen Mi
(74) *Attorney, Agent, or Firm* — Whitham Curtis Christofferson & Cook, PC

(57) ABSTRACT

A botanical composition made from a plurality of plant materials selected from Gota Kola (*Centella asiatica*), Turmeric Root (*Curcuma longa*), White Willow (*Salix alba*), Rosehips (*Rosa canina*), Hibiscus (*Hibiscus sabdariffa*), Evening Primrose (*Oenothera biennis*), and Bilberry (*Vaccinium myrtillus*), or phytochemicals or extracts or oils derived from the plant materials has beneficial application in addressing retinopathy and recurring peripheral neuropathy. The botanical composition can include a number of additional agents such as antioxidants, benfotiamine, thiamine (vitamin B1), and lipoic acid.

20 Claims, 1 Drawing Sheet

Figure 1. Gene Array Heat Map

|   | 1 | 2 | 3 | 4 | 5 | 6 | 7 | 8 | 9 | 10 | 11 | 12 |
|---|---|---|---|---|---|---|---|---|---|---|---|---|
| A | Abcb1a | Abcb1b | Abcb4 | Abcc1 | Abp1 | Adh1 | Adh4 | Adh5 | Ahr | Alad | Aldh1a1 | Alox12 |
|   | 3.1 | 0.57 | 1.69 | 0.63 | 2.31 | 4.8 | 2.04 | 1.47 | 2.66 | 0.38 | 4.07 | 0.58 |
| B | Alox15 | Alox5 | Apoe | Arnt | Asna1 | Blvra | Blvrb | Ces1g | Ces2c | Chst1 | Comt | Cyb5r3 |
|   | 0.99 | 1.07 | 3.52 | 0.38 | 1.68 | 2.18 | 2.02 | 1.69 | 4.48 | 1.57 | 0.7 | 0.66 |
| C | Cyp11b2 | Cyp17a1 | Cyp19a1 | Cyp1a1 | Cyp1a2 | Cyp27b1 | Cyp2b10 | Cyp2c29 | Cyp2e1 | Cyp4b1 | Ephx1 | Faah |
|   | 0.92 | 1.69 | 1.69 | 0.72 | 0.8 | 0.92 | 2.14 | 1.69 | 1.69 | 1.43 | 1.7 | 1.58 |
| D | Fbp1 | Gad1 | Gad2 | Gckr | Ggt1 | Gpi1 | Gpx1 | Gpx2 | Gpx3 | Gpx5 | Gsr | Gsta1 |
|   | 1.69 | 1.69 | 1.69 | 2.32 | 1.74 | 1.29 | 1.88 | 0.85 | 0.2 | 1.69 | 1.05 | 12.27 |
| E | Gsta3 | Gsta4 | Gstm1 | Gstm2 | Gstm3 | Gstm4 | Gstm5 | Gstp1 | Gstt1 | Gstz1 | Hk2 | Hsd17b1 |
|   | 3.43 | 1.52 | 1.04 | 1.15 | 1.48 | 1.26 | 2.46 | 16.44 | 1.04 | 1.66 | 2.53 | 0.75 |
| F | Hsd17b2 | Hsd17b3 | Lpo | Marcks | Mgst1 | Mgst2 | Mgst3 | Mpo | Mt2 | Mt3 | Mthfr | Nat1 |
|   | 0.59 | 1.69 | 1.69 | 0.66 | 3.68 | 1.92 | 1.61 | 1.69 | 0.98 | 2.74 | 1.1 | 1.69 |
| G | Nat2 | Nos3 | Nqo1 | Pklr | Pkm2 | Pon1 | Pon2 | Pon3 | Smarcal1 | Snn | Srd5a1 | Srd5a2 |
|   | 2.14 | 1.21 | 2.32 | 1.05 | 0.69 | 1.45 | 1.58 | 1.01 | 0.32 | 0.33 | 1.4 | 2.6 |

Fold Change

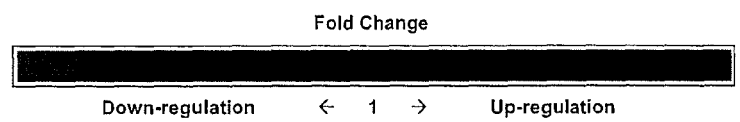

Down-regulation ← 1 → Up-regulation

Figure 2. Example and illustration of gene expression fold change from cells dosed with a botanical composition.

| Cyp1a1 | Cytochrome P450, family 1, subfamily a, polypeptide 1 | 0.72 |
|---|---|---|
| Gckr | Glucokinase regulatory protein | 2.32 |
| Gpx1 | Glutathione peroxidase 1 | 1.88 |
| Gpx3 | Glutathione peroxidase 3 | 0.20 |
| Gsta1 | Glutathione S-transferase, alpha 1 (Ya) | 12.27 |
| Gsta3 | Glutathione S-transferase, alpha 3 | 3.43 |
| Gstm5 | Glutathione S-transferase, mu 5 | 2.46 |
| Hk2 | Hexokinase 2 | 2.53 |
| Marcks | Myristoylated alanine rich protein kinase C substrate | 0.66 |

*Numbers greater than 1.0 indicate an increase in gene expression, while numbers less than 1.0 correspond to a decrease in gene expression. $P<0.05$ vs. control*

BOTANICAL COMPOSITION AND METHOD FOR TREATING PAIN AND DISCOMFORT OF VARIOUS CONDITIONS

CROSS-REFERENCE TO RELATED APPLICATIONS

This application is a continuation application of U.S. patent application Ser. No. 13/933,764 filed on Jul. 2, 2013 (now issued as U.S. Pat. No. 9,040,099), which is a continuation-in-part (CIP) application of U.S. patent application Ser. No. 13/287,168 filed Nov. 2, 2011 (now issued as U.S. Pat. No. 8,501,248), and a CIP application of U.S. patent application Ser. No. 13/834,018 filed Mar. 15, 2013, and also claims priority to U.S. Provisional Patent Application 61/409,305, "Novel Combinatorial Treatment for the Symptoms of Recurring Peripheral Neuropathy" filed on Nov. 2, 2010, and the complete contents of these applications is herein incorporated by reference.

FIELD OF THE INVENTION

The invention is generally related to botanical compositions and their use in medical treatments, and is particularly directed to the use of botanical compositions in management of pain and discomfort associated with various conditions including without limitation the symptoms of recurring peripheral neuropathy and retinopathy.

BACKGROUND

Modern Western medicines typically consist of a single, purified chemical entity administered to a patient to mediate a specific biochemical pathway. In contrast, many non-Western medicinal compounds that are used by many traditional cultures around the globe are often comprised of several botanicals and botanical extracts. Based on a pharmacognosy with several long-standing pharmacopeias effective in treating a wide range of diseases and their symptoms, these traditional compositions typically include a multiplicity of minimally-processed, naturally occurring ingredients. Composed without the benefit of modern clinical and scientific theory and knowledge, these traditional compositions were often derived from empiric observations in humans over the millennia. Yet, nevertheless, they often contain several biologically active, phytochemical components that act simultaneously and synergistically on multiple molecular targets and cellular mechanisms.

In recent decades in the United States, the active compounds in botanicals and phytochemicals derived from plant extracts have become an area of interest for treating diseases and their symptoms by both healthcare professionals and patients alike. There are many documented examples of this in contemporary scientific, clinical and lay literatures, and in the USPTO patent archive. These is also interest in compositions that combine one or more botanical extracts with one or more other medicinal compounds, pharmaceuticals or other synthetic chemical entities. Some of these compositions are intended to potentiate or modify specific therapeutic effects. In the United States, many of these medicinal compositions are widely used and are commercially available as over-the-counter dietary supplements that do not require a physician's prescription. In some cases, such compounds are available only with a physician's prescription.

The National Institutes of Health (NIH) estimate three out of five U.S. consumers take dietary supplements or nutritional products on a regular daily basis to maintain good health. This is due in large part to demographics, as aging Baby Boomers strive to stay healthy based on the belief that proper nutritional supplementation can avert, or in some instances even replace, the need for costlier prescription drugs and treatments, especially if one has a chronic disease condition. For example, the American Diabetes Foundation, reports that patients with diabetes are 1.6 times more likely than patients without diabetes to use complementary medicinal products such as herbal treatments, nutritional products and medical foods. The Foundation estimates that 17-30% of all diabetics routinely use health care supplements and/or alternatives to prescription pharmaceutical use. Some of these are used to improve blood glucose control; others to manage various symptoms or lessen the risk of developing serious, later-stage diabetic complications.

An example of a dietary supplement aimed at combating pain and inflammation in joints and connective tissue is Bio-inflammatory Plus™, a product which includes White Willow Bark in a powder supplement, and Turmeric root in a capsule formulation. These formulations combine a number of ingredients; however, they do not show combining specific botanicals to achieve beneficial effects in addressing recurring peripheral neuropathy or retinopathy.

The USPTO has granted patents for complex herbal compositions and novel formulations used to treat various human and animal diseases and their associated symptoms. These include novel compounds that have been extracted from natural botanical sources and/or synthesized chemically; in some cases the novel compounds are complex combinatorial compositions of several botanicals in combination with synthetic chemical ingredients. These herbal compositions and formulations have targeted a variety of acute and chronic diseases and symptoms, including specific diseases such as various types of cancer, diabetes and arthritis. These herbal compositions and formulations also target various types of symptoms clinically associated with various diseases, as well as symptoms from down-stream sequelae, side effects and adverse events causally related to physician administered or prescribed medications. Examples of patents issued by the USPTO for botanical compositions and formulations used for the treatment include both acute and chronic diseases range from viral infections to cancer, diabetes and arthritis and various symptoms associated a disease include but are not limited to (each of which are herein incorporated by reference): treating glioblastomas with a complex herbal composition that includes modulating gene expression (U.S. Pat. No. 7,931,922); a herbal composition and method for combating inflammation (U.S. Pat. No. 6,541,045); the treatment of ocular inflammation with a composition containing the plant-based alkaloid, tetrandrine (U.S. Pat. No. 5,627,195); a complex composition of multiple botanical ingredients targeting inflammation and related symptoms (U.S. Pat. No. 5,683,697); a composition comprising a mixture of herbs, including species of *Scutellaria barbata*, as well as their extracts, which is used to ameliorate the effects of malignancy in humans (U.S. Pat. No. 5,437,866); and a formulation of various herbal ingredients which include *Glycyrrhiza glabra* L. and *Scutellaria baicalensis* Georgi, *Rabdosia rubescens*, and *Serenoa repens* for the treatment of prostate carcinoma (U.S. Pat. No. 5,665,393).

SUMMARY

The present invention is in the technical field of disease and symptom treatment. More particularly, the present invention is in the technical field of using a mixture of specific compounds to treat specific symptoms of pain and/or discomfort related to specific disease states. An embodiment of the invention provides a botanical, phytochemical and medicinal composition and method useful for reducing the pain and discomfort symptoms of recurring peripheral neuropathy related to diabetes, as well as the treatment of the peripheral neuropathic side effects resulting from the use of various chemotherapies related to the treatment of specific neoplasms of cancer, and the use of various anti-viral treatments related to the treatment of HIV-AIDs. Another embodiment of the invention provides a composition and method for slowing the progression of retinopathy and/or age-related macular degeneration (e.g., the rate of decline may be abated or slowed through regular dosing). The compositions and methods described herein are for improving the quality of life of an individual. Based on its composition of exogenous antioxidants and other nutrients, the compositions and methods described herein provide multi-faceted therapeutic effects, and significant free radical scavenging abilities beneficial against oxidative stress damage to nerve, vascular, endothelial tissues, and lipid-based cell membranes and other lypophilic structures.

Aspects of the invention relate to a novel formulation and method for relieving the pain and discomfort of peripheral neuropathy as well as modulating other significant adverse disease effects attributed to toxicities and cellular signaling derangements signaling caused by reactive oxygen species (ROS) and reactive nitrogen species (RNS). ROS and RNS act as free radicals and, if not readily detoxified, they can accumulate in bodily tissues and cause oxidative stress, an eminent factor in many diseases and their related symptoms. Common ROS include super oxide ($O^{2-}$), hydroxyl radicals such as hydroxide (OFF), and hydrogen peroxide ($H_2O_2$). These often form as a normal byproduct of oxygen metabolism. Their highly reactive biochemical nature is due to the presence of unpaired valence shell electrons. In mammals, ROS and RNS effectively function as toxic signaling molecules, activating a number of stress-sensitive, cellular signaling pathways that, in turn, cause damage to various biologically important macromolecules and critical cellular structures.

Many scientists believe that these derangements in cellular signaling due to oxidative stress caused by ROS and RNS are material contributing factors to many chronic disease conditions and their down-stream complications, such as diabetes and its down-stream sequelae that include both peripheral neuropathy and retinopathy. Though not completely understood due to the number of pathways involved, researchers have demonstrated that as reactive species cascade across adjacent cells and cellular membranes, they induce the formation of powerful, reactive compounds that are potentially cytotoxic, mutagenic and carcinogenic. Some of these reactive compounds have profoundly toxic effects on polyunsaturated fatty acids in lipid membranes and on carbohydrates, proteins, and nucleotides. In addition, the reactive compounds have harmful effects on a multiplicity of other biologically important organic compounds, such as estrogens, catecholamines, furans, retinoids, and dietary phenols. In response, humans and other organisms have developed a complex, endogenous anti-oxidant defense system, including many xenobiotic metabolizing enzymes.

Many botanical preparations contain abundant compounds that have the ability to scavenge free radicals including various forms of polyphenols, glycosides, saponins, bio-flavonoids, and triterpenes among other phytochemicals. In addition, many of these types of phytochemicals exhibit a range of biological activities in humans and mammals such as inducing vasodilation and immune response, or exhibiting allergic, antiviral, anti-bacterial and estrogenic effects. Some of these botanical phytochemicals can also act as agonists or antagonists of specific enzymes such phospholipase A2, cyclooxygenase, and lipoxygenase. Moreover, many of the plant flavonoids, phenolics or other phytochemicals do not act directly on a specific enzymatic process; rather they act indirectly by activating or de-activating related cellular stress-sensitive signaling pathways.

Examples of the most common disease states and/or treatments addressed by specific embodiments of the invention include diabetes and its complications, notably diabetic peripheral neuropathy (DPN) and retinopathy; the side effects of specific cancer chemotherapies administered to various types of cancer patients; and the side effects of various anti-viral therapies administered to HIV-AIDS patients.

Type II diabetes has become a global epidemic. Often characterized as adult-onset diabetes, Type II diabetes is now being seen in younger patients. According to estimates from national health experts, the total number of Americans with Type II diabetes will double over the next two decades; from the current 23.7 million to an estimated 44 million by 2034. During that same time frame, annual costs for treating those patients are expected to soar—nearly tripling from the current $113 billion to some $336 billion. The average annual health care costs in 2009 for a person with known diabetes were about $11,700 compared with about $4,400 for the non-diabetic public, according to data from United Healthcare, one of the largest health insurers. The average annual cost nearly doubles to $20,700 for a person with complications related to diabetes; complications related to diabetes can include heart and kidney disease, nerve damage and neuropathy, retinopathy leading to blindness and other similar problems. According to NIH, peripheral neuropathy (PN) is one of the most common complications of diabetes, symptomatically manifest in an estimated sixty to seventy percent (60-70%) of all diabetes patients. As a debilitating sequelae of diabetes, patients experience diabetic peripheral neuropathy (DPN) as varying sensations of pain, often described as a combination of burning, tingling, stabbing, shooting pain and/or hypersensitivity discomfort in peripheral extremities, most often in the feet and hands.

Without intending to be bound by theory, several clinical researchers have postulated that DPN results from a cascading sequence of events initiated by an hyperglycemic overload in cytoplasmic fluids and surrounding tissues that, in turn, triggers an exaggerated release of multiple, overlapping cytokines (small, cell-signaling protein molecules generated by cytokine genes that are used extensively in intercellular communication) and other signaling molecules. This exaggerated cytokine release is a type of traumatic response against the extraordinary albeit potentially cytotoxic oxidative insult from excessive, non-ezymatically processed, local intra-cellular glucose which is interpreted by the immune system as a new, highly pathogenic invader that can do significant damage to body tissues and organs. Induced by the initial glucose insult and the cytokine-mediated oxidative stress response—and instead of acting to reduce the resultant oxidative stress—the inflammatory cytokines cascade further, triggering the release of additional other often conflicting cytokines and chemokines (hypercytokinemia), sometimes called a cytokine storm, further compounding the level of oxidative stress. One downstream effect of this exaggerated cytokine response, and disruption in various cellular signaling pathways, is a derangement to the sorbitol pathway, which can create significant damage to local endothelial and epithelial cells and often, potentially, to larger organs and organ systems as well. Again, without intending to be bound by theory, many researchers also believe this same type of oxidative stress reaction, and its sequelae, are linked to retinopathy of the eyes, a leading cause of blindness in diabetics. While both cytokines and hormones can be immunomodulating, cytokines and chemokines are distinguished from hormones in that the immunomodulating effects of cytokines are often local rather than systemic; in contrast, classic hormones, such as insulin, are secreted from discrete glands (e.g., the pancreas) and act systemically.

Virtually all nucleated cells, but especially endothelial cells, epithelial cells and resident macrophages (many near the interface with the external environment, including those involved with epithelioid cells, the retina, and connective and nerve tissues) are potent producers of Interleukin 1 beta (IL-1β), Interleukin-6 (IL-6), Tumor Necrosis Factor alpha (TNF-α) and other biologically critical cytokines, chemokines and signaling molecules active in cellular immune response function, whether agonist or antagonist, and whether pro-inflammatory or anti-inflammatory. IL-6 regulation may be of particular importance to embodiments of this invention since it is a cytokine that is involved in many cell signaling pathways. Like other cytokines, IL-6 is, or can be stimulated to be produced, by many different cell types, including normal cell types, as well as types of several tumor cells. Like other cytokines, IL-6 is multi-modal and can act as an agonist and/or antagonist; even, in some types of cells, regulating its own production. Scientists recognize that IL-6 has several critical biological functions, most notably enhancing, suppressing or preventing immune and inflammatory responses. It can also induce specific cells to differentiate, or secrete antibodies, or induce various cell signaling factors.

Since each cytokine and chemokine has a matching cell-surface receptor, during an episode of DPN, an uncontrolled, conflicting cascade of intracellular signaling by cytokines and chemokines violently alters cell function and immune response; a type of feedback overload message that is experienced as shifting types of pain, pins and needle tingling, and burning sensations or discomfort. This cytokine production process also involves the up- and down-regulation of several genes and their transcription factors, triggering an increase in the number of cell surface receptors for other molecules and the suppression of normal, inhibitory feedback. During the DPN cascade, researchers estimate circulating cytokines and chemokines increase exponentially, perhaps several hundred fold or even a 1,000-fold or more, easily overwhelming endogenous anti-oxidant defenses. The present invention is highly lipophilic and consists of several synergistic, multi-faceted, potent exogenous antioxidants, and other supporting nutrient compounds that materially blocks the pro-inflammatory roles of IL-6 and other material cytokines and induces anti-inflammatory responses.

Beyond its action on IL-6, embodiments of the invention inhibits and/or mediates a range of cellular inflammatory signaling processes and specific stress-response enzymes and anti-oxidant defense proteins, including specific cytokines, chemokines, detoxifying enzymes and gene expression of selected genes. In vitro, in various non-toxic and increasing concentrations applied to multiple, in-vitro, cultured human Retinal Pigmentation Epithelial (RPE) cell models, which were exposed to increasing levels of ROS and RNS stress, a formulation prepared according to an embodiment of the present invention was shown to be able to significantly reduce and, in some concentrations, completely block the $H_2O_2$-induced increase of IL-6 as well as the secretion of Interleukin 1β (IL-1β) by the human RPE cells in vitro. Human RPEs are a single layer of pigmented cells located in the eye, between the neural retina and the choroid. RPE cells have multiple functions essential to the maintenance of the overlying photoreceptors and visual function. Disturbance of functions of RPE cells plays an important role in various eye diseases. Both IL-1β and IL-6 can act as pro-inflammatory cytokines and play a role in the occurrence of auto-immune diseases. Increase of circulating and locally produced pro-inflammatory cytokines is associated with various complications of diabetes, including diabetic retinopathy, diabetic neuropathy and diabetic nephropathy.

A formulation prepared according to an embodiment of the invention also has been shown in murine cell models to be a potent mediator capable of inducing quinone reductase 1 (QR-1) and other phase II detoxifying enzymes. As a result, and without intending to be bound by theory, the invention likely induces expression of other endogenous signaling molecules and their effects, such as heme oxygenase-1 (HO-1), a stress-response enzyme and antioxidant defense protein found in intracellular fluid; it also likely induces anti-inflammatory effects via a p38 mitogen-activated protein kinase-dependent pathway.

By design, a composition within the scope of the present invention includes small amounts of specific raw botanicals. These can, in some embodiments, be intentionally combined with specifically matched botanical extracts or oils or phytochemicals from the same plant (i.e., a matched ingredient) to activate and potentiate an overall larger synergistic, therapeutic effect. The raw botanicals can be from any portion of the plant, and exemplary compositions could have one or more than one matched ingredients (e.g., 2-7 or more plant materials plus 1-3 matched ingredients which are matched to 1-3 of the 3-7 plant materials, and example being Evening Primrose plant material (e.g., leaf), Evening Primrose oil, and Bilberry plant material (e.g., fruit or leaf)). Botanists have identified many but not all phytochemicals and co-factors in the specific botanicals described herein, and without being bound by theory, some portion of the therapeutic benefits of embodiments of the invention may be attributed to the synergistic actions of many of these unidentified phytochemicals. These botanical combinations can be combined with synthetic medicinal chemicals and nutrients. In addition, these botanical combinations can be combined with a specific group of plant-derived oils, as well as many other ingredients.

In embodiments of the invention a specific mixture of plant-derived oils are provided and act as a lypophilic carrier for the other active ingredients and compounds in the composition. This mixture of plant-derived oils may also contain bioavailable Essential Fatty Acids (EFAs) such as linoleic acid (LA): an essential fatty acid from which the human body makes several derivative essential fatty acid compounds, including gamma-linolenic acid (GLA) and dihomogamma-linolenic acid (DGLA). By specifically by elevating DGLA, the present invention increases the body's innate production of Prostaglandin E1 (PGE1), an eicosanoid hormone made from fats which lowers cardiovascular risk factors and is an essential factor for decreasing inflammation in the body. Researchers have established that DGLA also increases Prostacyclin 12 (PG12; combined, PGE1 and PG12 dilate small blood vessels and act to increase blood supply to tissues and reduce inflammation pain. The present invention may reduce the production of Thromboxane B2 (TxB2); resulting in a decrease human platelet aggregation, reducing the blood's clotting tendency. Inhibitors of this TxB2 enzyme seem to prevent the development of neuropathy, nephropathy, retinopathy, and cataract formation in mammals. Compositions within the scope of the invention may also impact the polyol pathway (also called the sorbitol-aldose reductase pathway).

This is a significant mechanism mediated by embodiments of the present invention, since the polyol pathway is thought to be major contributor to microvascular and nerve-related diabetic complications. When intracellular glucose rises, aldose reductase activity is stimulated. The aldose reductase, in turn, catalyzes the formation of sorbitol, which is then oxidized to fructose by sorbitol dehydrogenase, another enzyme present in human cellular response mechanisms. As sorbitol accumulates at an intracellular level, it causes cell damage and deranges other stress-sensitive cellular signaling sequences that are potentiated by sorbitol, such as the p38 mitogen activated protein kinase (MAPK) and JNK pathways.

As recurring high glucose in concert with free fatty acids increases production of ROS and RNS, and DNA, proteins, lipids, and stress-sensitive cellular signaling pathways are subjected to damage, it is thought that human cellular mitochondria also contribute to the domino-like pathogenic processes. It is well-known that mitochondria produce a large part of the total ROS made in cells, often resulting in excessive amounts of ROS in skeletal and other tissues. The essential fatty acids (EFAs) and other ingredients in the present invention potentially modulate this mitochondria effect by helping to activate a proton pathway in the inner mitochondrial membranes involved with uncoupling proteins (UCPs): a small family of proteins identified by scientists that play a vital role cell metabolism as anion mitochondrial transporters.

Clinical researchers believe that the distribution of several types of UCPs across different tissues suggests they likely have multiple, albeit unknown, metabolic and biologic roles, beyond mediating the in- and out-bound transport of protonated fatty acids across cell membranes. Several independent studies suggest the UCPs are part of our bodies' intrinsic defense mediating oxidative stress. We propose that the novel combination of ingredients in a composition according to an embodiment of the present invention may act as a protective antagonist or agonist, up and down-regulating specific metabolic pathways critical to UCP activity vis-a vis sensitive tissues affected by DPN.

In patients with diabetic complications, glucose-induced oxidative stress triggers a complex flood of cytokines and chemokines, triggering a metabolic signaling pathway breakdown and immune system over-reaction and derangement. The sequelae of this process is inflammation of sensitive tissues, often typically clinically manifest as DPN with its signature painful, tingling, burning symptoms in the hands and feet. Clinical research has demonstrated that a formulation according to the present invention significantly reduced, and in some cases, eliminated the oxidative stress, caused by ROS and RNS. In addition, in an initial single patient trial, repeatedly over a period of more than six months (and with an onset of therapeutic effect within 45 minutes (e.g., less than one hour)), the inventive composition significantly reduced and/or eliminated the pain and discomfort associated with DPN.

The present invention further addresses chemotherapy-related peripheral neuropathies. Cancer is the second overall cause of death in the United States. Current chemotherapy protocols for treating cancer usually consist of administering a single antineoplastic agent or combination therapy of several agents. These antineoplastic regimens can cause severe toxicity reactions in patients, including neurologic complications such as peripheral neuropathy. These neuropathic complications are thought to arise from direct toxic effects of antineoplastic drugs on the nervous system and from chemotherapeutic drug-induced metabolic derangements resulting in significant ROS and RNS.

Based on the clinical research performed in murine-based cancer models, a composition according to an embodiment of the present invention has been shown to be effective in the up- and down regulation of various genes, and cytokines and chemokines associated with cancer-related ROS and RNS. Based on this research vis-a-vis the invention's mechanisms of action, the invention is likely beneficial in alleviating those peripheral neuropathies and nephrotoxicities associated with several commonly used chemotherapies, including but not limited to the entire class of platinum-based chemotherapies. Among these platinum analogue based compounds, specifically, cisplatin and oxaliplatin are most commonly linked to patient complaints of various forms of peripheral neuropathy. Peripheral neuropathy is also associated with the cancer chemotherapy drug paciltaxel: a mitotic inhibitor (stops the cancer cells from multiplying into new cells) used in the case of ovarian, breast, non-small cell lung cancer and other cancers. A review of the literature suggests that several related antineoplastic agents and other medications are potentially equally neurotoxic and may cause various peripheral neuropathies. In recent years, researchers and physicians have sought effective therapeutic agents to either prevent or limit the symptoms associated with chemotherapy-induced peripheral neuropathy, including but not limited to amifostine, diethyldithiocarbamate, glutathione, and Vitamin E.

Embodiments of the present invention address several types of peripheral neuropathy associated with HIV-AIDs patients called HIV sensory neuropathy (HIV-SN), distal sensory polyneuropathy (DSP) and anti-retroviral (ARV) toxic neuropathy. Collectively, these conditions present clinically with symptoms of bilateral tingling, numbness, and other types of neuropathic pain starting in their toes and spreading proximally; the pain frequently is described as burning or aching or knife-like and is worse on the soles. It is indistinguishable from other toxic neuropathies. HIV-SN is a "dying-back" neuropathy that affects the most distal fibers first, involving both myelinated and unmyelinated axons of all sizes. The HIV-SN includes: (1) DSP caused by HIV infection itself; (2) Toxic neuropathy resulting from exposure to ARVs, particularly d4T, ddI, and ddC (the "dNRTIs" or "d-drugs"). The onset can occur as early as nine weeks after starting the first round of ARV therapy. It is thought to be related to chronic immune activation, leading to macrophage overproduction of proinflammatory cytokines and chemokines in the peripheral nervous system. Similarly, ARV toxic neuropathy is thought to be associated with derangements to mitochondrial structures as caused by the toxic effects of the dNRTIs. A recent study showed the prevalence of HIV-SN was 42% among HIV-AIDS patients and up to 92% of patients with sensory neuropathy were on ARVs. Apparently, the risk of PN is higher for patients with advanced HIV infection and the prevalence is lower among patients with less-advanced HIV disease. Typically treatment protocols treat suspected ARV toxic neuropathy by withdrawing or reducing the offending ARV drug. First line therapies for treating the pain of HIV-SN includes analgesics, anticonvulsants, topical medications, and even long-acting narcotics.

Embodiments of the invention may be of benefit in managing the negative impacts of oxidative stress across a variety of other diseases conditions and their symptoms beyond peripheral neuropathy. Each ingredient in the invention, and the invention as a whole, possess a distinct pharmacological profile that includes but is not limited to one or more of the following properties: anti-inflammatory and anti-oxidative stress properties, immunological and gene regulation, and peripheral neuropathy pain and discomfort symptom relief. Without intending to be bound by theory, embodiments of the invention also likely beneficially affects other parts of the cellular signal transduction system, enabling humans and mammals to respond to a wide range of epigenetic oxidative stressors and conditions. Aspects of the present invention inhibit oxidative stress, which in turn benefits a subject's health and general well-being, and in particular, mitigates the symptomatic pain and discomfort of peripheral neuropathy (PN). Again, without intending to be bound by theory, the invention's novel composition of botanicals, extracts and other compounds may directly or indirectly increase the levels anti-inflammatory genes and cytokines, decrease the levels of pro-inflammatory genes and cytokines, and help mediate aspects of cellular signaling degeneration in chronic disease, as well as in other conditions, disorders and disease treatments that have been reported to be associated with higher than normal levels of oxidative stress from ROS and RNS. Such conditions, disorders and diseases include cardiac disorders, atherosclerosis, neurodegenerative disorders, diabetes and cancer, HIV-AIDs, as well as specific antineoplastic treatments for various cancers and specific anti-retroviral treatments for HIV-AIDs.

According to the invention, a novel composition and method that combines individual botanicals, phytochemicals, phytochemical extracts, nutrients and medicinal chemical compounds not found in nature has been found to reduce oxidative stress, and has particular application to addressing retinopathy and recurring peripheral neuropathy (and may address both problems simultaneously). The combination of exogenous ingredients produces a synergistic effect/action not previously known in the treatment of the symptoms of recurring peripheral neuropathy (e.g., pain and discomfort) and disease conditions of similar etiology, such as retinopathy. Peripheral neuropathy and its symptoms are the most common peripheral nerve complication of diabetes, affecting up to sixty percent of all diabetics. Without intending to be bound by theory, it is thought that these debilitating sequelae of diabetes are due to prolonged oxidative stress from ROS and RNS, caused by over exposure to excessive tissue levels of glucose. In these diabetic complications, glucose-induced oxidative stress triggers a complex flood of cytokines and chemokines, triggering a metabolic signaling pathway breakdown and immune system over-reaction and derangement. The sequelae of this process is inflammation of sensitive tissues, typically clinically manifest as DPN with its signature painful, tingling, burning symptoms in the hands and feet. Similarly, without intending to be bound by theory, many researchers believe this same type of oxidative stress reaction, and its sequelae, are linked to retinopathy of the eyes, a leading cause of blindness in diabetics. Again, similarly, without intending to be bound by theory, many researchers also believe this same type of oxidative stress reaction, and its sequelae, are linked to the neuropathy side effects associated with various cancer chemotherapies and HIV AIDS treatments. Experimental results with compositions according to the invention demonstrated significantly reduced, and in some cases, eliminated the oxidative stress, caused by ROS and RNS. In a diabetic individual with moderate to severe DPN, the invention repeatedly, and with a short onset of action, vastly reduced and/or eliminated the symptoms of pain and discomfort.

The dosage ranges for the compositions of the present invention are those large enough to produce the desired therapeutic outcome. Preferably, the compositions of the present invention are administered one or more times per day on a regular basis. A typical dose administered to a human may be between about 500 mg and about 5 g, preferably between 750 mg and 2 g of the combination of the raw plant materials, active botanical extracts, carrier oils, and nutrients. Those skilled in the art will recognize that initial indications of the appropriate beneficial amounts (e.g., therapeutic amounts) of the compositions of the invention can be determined in in vitro and in vivo animal model systems, and in human clinical trials. One of skill in the art would know to use in vitro studies and human experience to identify a dosage that can safely be administered without generating toxicity or other side effects. For acute treatment where it is desirable to substantially decrease the free-radical and oxidative stress linked to peripheral neuropathy and related symptoms, it is preferred that the beneficial dosage be close to the maximum tolerated dose. For chronic preventive use, lower dosages may be desirable because of concerns about long term effects. However, the active botanical extracts, oil carriers, nutrients of the present invention, are commonly believed to be safe. The compositions may be taken or administered one or more times per day.

In an embodiment of the invention, a composition for treating the symptoms of sensory pain and discomfort associated with Diabetic Peripheral Neuropathy (DPN) would comprise one or more plant parts (roots, leaves, bark, fruit, essential oils, shoots, flowers or other) that deliver therapeutically effective amounts of bilberry (*Vaccinium myrtillus*) from amounts about 0.01 to 90% by weight, and more preferably from about 10% to about 40% by weight, evening primrose leaf (*Oenothera biennis*) from amounts about 0.01 to 90% by weight, and more preferably from about 20% to about 60% by weight, and Tumeric root (*Curcuma longa*) from amounts about 0.01 to 90% by weight, and more preferably from about 10% to about 40% by weight. In an embodiment, the composition could comprise white willow bark (*Salix alba*) from amounts about 0.01 to 90% by weight, and more preferably from about 20% to about 60% by weight. In an alternative embodiment or in addition to white will bark, the composition could also include gotu kola (Centella *asiatica*) from amounts about 0.01 to 90% by weight, and more preferably from about 20% to about 40% by weight. In an embodiment, the composition may also include rosehips (*Rosa canina*) from amounts about 0.01 to 90% by weight, and more preferably from about 20% to about 40% by weight. In another embodiment, the composition may also include. hibiscus (*Hibiscus sabdariffa*) from amounts about 0.01 to 90% by weight, and more preferably from about 20% to about 40% by weight. In another embodiment, the composition may include sea buckthorn (*Hippophae rhamnoides*) from amounts about 0.01 to 90% by weight. In various embodiments, the composition may be modified by adding one or more, in various ratios and by weight, of therapeutically effective amounts of extracts derived from *Centella asiatica, Curcuma longa, Salix alba, Rosa canina, Hibiscus sabdariffa, Oenothera biennis*, and *Vaccinium myrtillus*. In various embodiments, the composition may be modified by adding therapeutically effective amounts of different forms of Vitamin B1 Thiamine which is water soluble, or its derivative Benfotiamine (S-benzoylthiamine O-monophoshate). Biotin and/or Taurine (2-aminomethanesulphonic acid) may also be included in therapeutically effective amounts in the composition. Similarly, the composition may be modified by adding therapeutically effective amounts of different forms of lipoic acid, be it alpha lipoic acid, s-alpha lipoic acid or r-alpha lipoic acid. The composition may also be modified by adding one or more therapeutically effective amounts of with oil extracts derived from plant parts and plant seeds, in various ratios and by weight, including preferably one or more plant part and plant-seed derived oils that, in some embodiments, that may act as a lypophilic carrier for the other active ingredients and compound. The compositions may also contain bioavailable Essential Fatty Acids (EFAs) such as linoleic acid (LA): an essential n-6 fatty acid from which the human body makes several derivative essential fatty acid compounds, including gamma-linolenic acid (GLA) and dihomogamma-linolenic acid (DGLA), including more preferably, in various ratios and by weight, one or more plant-derived oils from *Cannabis sativa, Camelina sativa, Oenothera biennis,* and *Hippophae rhamnoides*. The compositions may further comprise one or more therapeutically effective amounts of with minerals deemed essential for human metabolism and health, in various ratios and by weight, and in any form, including preferably Magnesium, Zinc, Chromium, and Selenium.

DESCRIPTION OF THE DRAWINGS

FIG. 1 is an example of gene heat array map which may be used in the practice of the invention which shows the upregulation and downregulation of a plurality of genes; and FIG. 2 is an example of a tabular presentation of genes which can be used as an alternative to the gene heat array map shown in FIG. 1 or in addition to the gene heat array map where the table illustrates the gene expression fold change for cells dosed with a botanical composition

DETAILED DESCRIPTION

With respect to the invention described herein, the following terms can best be understood with reference to the definitions below.

The term "extract" as used herein refers to a functional end product made by means of a process of drawing out, withdrawing, distilling or otherwise separating one substance from another by a chemical or physical process.

The terms "phytochemical" and "active constituent" are defined as the chemical constituent in a botanical raw material or botanical extract or in a nutrient that is responsible for the intended therapeutic effect.

The term "botanical ingredient" refers to a component that originates from a botanical raw material.

The term "plant materials" refers to the bark, root, leaves, flower, seed, seed-based oil, or any other part of a plant.

The term "botanical product" or "botanical composition" refers to a finished, labeled product that contains vegetable matter, which may derived from any part of a plant or plant material, or combinations thereof. Depending in part on its intended use, a botanical product/botanical composition may be a food, drug, medical food, dietary supplement, medicinal supplement, nutritional supplement, nutritional or nutrient. The botanical product/botanical composition can include a number of additional agents.

The term "botanical extract" as used herein refers to a product prepared by separating, by chemical or physical process, any medicinally active portions of a plant from the inactive or inert components. The botanical extracts prepared according to the present invention preferably are obtained by means of a polar solvent, or optionally, under pressure and/or heat.

The terms "dietary supplement" and "medicinal supplement" and "medicinal food" and "nutritional supplement" and "nutritional" and "nutrient" are used interchangeably herein to mean a product intended to supplement the diet that bears or contains one or more of the following dietary ingredients: (1) a vitamin in any form, (2) a mineral in any form, (3) an herb or other botanical in any form, (4) an botanical extract in any form, (5) a synthetic chemical molecular entity that is bioactive, and generally recognized as safe, (6) a dietary substance for use by man, either found in nature or not, designed to supplement the diet by increasing the total dietary intake; and/or (7) a concentrate, metabolite, constituent, extract, or combination of any ingredient described in clause (1), (2), (3), (4), (5), (6), and/or (7); and/or a product that is intended to be ingested, is not represented for use as a conventional food or as a sole item of a meal or the diet, and is labeled as a dietary supplement, and generally recognized as safe, under FDA mandate. For purposes of the present invention, the terms also include foods and beverages and dietary and nutritional supplements that are supplemented or enhanced with the active botanical ingredients and/or extracts of the present invention.

The invention contemplates providing a patient with a botanical composition which includes a plurality of plant materials selected from Gota Kola (*Centella asiatica*), TurmericRoot (*Curcuma longa*), White Willow (*Salix alba*), Rosehips (*Rosa canina*), Hibiscus (*Hibiscus sabdariffa*), Evening Primrose (*Oenothera biennis*), and Bilberry (*Vaccinium myrtillus*). By plurality, it is meant that the composition will have at least two of the listed plant materials, and more preferably, 3, 4, 5, 6, or all 7 of the plant materials. By plant materials, it is meant that the bark, root, leaf, stem, flower, stamen, seed, or seed oil, or any other part of the plant may be used in the composition. For example, one may use White Willow Bark, Turmeric Root, and Evening Primrose Leaf. As will be discussed in more detail below, the activities of each of these botanicals can be potentiated by including oils formed from these same botanicals in the composition which will be administered to a subject (human or animal). For example, a composition according to the invention might include both Evening Primrose leaf and Evening Primrose oil. The composition may also include Bilberry leaf and an extract from Bilberry fruit.

The botanical composition may be formulated to include additional botanicals (e.g., hemp seed oil (*Cannabis sativa*), carmalina oil (*Carmelina sativa*), and sea buckthorn oil (*Hippophae rhamnodies*), etc.), as well as additional active agents.

In a particular embodiment, the botanical composition will include an antioxidant selected from n-acetylcysteine (NAC) and acetyl-L-carnitine, and at least one agent selected from benfotiamine, thiamine (vitamin B1), quercetin, and lipoic acid. It is well-known that N-acetyl-cysteine (NAC) promotes cellular glutathione production, and thus reduces, or even prevents, oxidant mediated damage. Treatment with NAC provides beneficial effects in a number of respiratory, cardiovascular, endocrine, infectious, and other disease settings. The lipoic acid is preferably in the form of r alpha-lipoic acid. Minerals such as magnesium, zinc, chromium, and selenium, etc., may also be included in the composition, as well as excipients such as beeswax, lecithin, and glycerin, etc., essential fatty acids, and biotin.

In yet another embodiment, the botanical composition will include Taurine (2-aminoethanesulphonic acid) which is a semi-essential amino widely available through dietary sources, primarily meat and fish. Taurine is found throughout the human body and is the most abundant free amino acide in the heart, retina, skeletal muscle, and leukocytes. Plasma levels of taurine vary greatly across individuals, and this is likely dependent on diet, genomic polymorphisms, and life style. The FDA has not yet approved taurine as a food additive; however, the Flavor and Extract Manufacturers Association of the United States generally recognizes it as safe for flavor use. Numerous studies suggest that taurine supplementation is beneficial in multiple ways. Most importantly, it has been shown to be highly protective against oxidative stress and related injuries in human tissues. Researchers have described various other roles for taurine on cellular functions.

These include but are not limited to: a neurotransmitter, an insulin sensitizer that may attenuate diabetes or its complications, a protector against cardiomyopathy, as well as an enabler of various mitochondrial activities. It is thought that taurine reacts with hypochorous acid (HOCl), produced by the myeloperoxidase (MPO) pathway, to produce the more stable taurine chloramines (Tau-Cl). Several studies demonstrate that Tau-Cl is a powerful regulator of the immune system. It has been shown to down-regulate the production of various proinflammatory mediators by multiple transcription and translational mechanisms. These mechanisms include inhibiting the activation of NFK$\beta$, a potent signal transducer for various inflammatory cytokines, including without limitation IL-1$\beta$, IL-6, IL-8, and TNF-$\alpha$. These regulatory effects on various inflammatory cytokines are similar to the demonstrated activities of the botanical compositions described herein. By adding taurine to the botanical compositions, the effects of the botanical compositions can be enhanced.

The composition can be formulated as an oral dosage form. In addition, an extract of all and/or a plurality of parts of the composition might also be provided to a subject. As will be discussed in more detail below, the composition will be particularly useful in treating subjects suffering from retinopathy or recurring peripheral neuropathy.

In a particular embodiment, the composition can be delivered in a specific combination as a medical food, a pharmaceutical, or as a nutritional supplement. The composition preferably has the following attributes: i) a pharmaceutically acceptable form; ii) a formulation of sufficient potency consisting essentially of one or more extracts, combinations and/or derived preparations of bioflavonoids, phytochemicals, preparations and/or anti-oxidants and their various forms, derived in whole or in part, from of any constituent, and of any combination of the plant species of: *Centella asiatica, Curcuma longa, Salix alba, Rosa canina, Hibiscus sabdariffa, Oenothera biennis, Vaccinium myrtillus*; iii) a formulation of sufficient potency consisting essentially of one or more extracts, combinations and/or derived preparations of bioflavonoids, phytochemicals, preparations and/or anti-oxidants and their various forms, derived in whole or in part, from of any constituent, and of any combination of the plant species of: *Centella asiatica, Curcuma longa, Salix alba, Rosa canina, Hibiscus sabdariffa, Oenothera biennis*, and *Vaccinium myrtillus*, delivered, in whole or in part, in combination with one or more other therapeutically bioactive compounds, including but not limited to vitamins, vitamin-derivatives, anti-oxidants and/or any anti-oxidant formulae, plant-derived oils, minerals, chemicals, medications, extracts of any kind and other similar ingredients; iv) a formulation of sufficient potency consisting essentially of one or more extracts, combinations and/or derived preparations of bioflavonoids, phytochemicals, preparations and/or anti-oxidants and their various forms, derived in whole or in part, from of any constituent, and of any combination of the plant species of: *Centella asiatica, Curcuma longa, Salix alba, Rosa canina, Hibiscus sabdariffa, Oenothera biennis*, and *Vaccinium myrtillus*, combined, in whole or in part, in a formulation with one or more the following other therapeutically bioactive compounds, consisting of N-Acetyl-L-Cysteine (NAC), Benfotiamine, Biotin, Quercetin and/or Alpha Lipoic Acid; v) a formulation of sufficient potency consisting essentially of one or more extracts, combinations and/or derived preparations of bioflavonoids, phytochemicals, preparations and/or anti-oxidants and their various forms, derived in whole or in part, from of any constituent, and of any combination of the plant species of: *Centella asiatica, Curcuma longa, Salix alba, Rosa canina, Hibiscus sabdariffa* and *Vaccinium myrtillus*, combined, in whole or in part, in a formulation with one or more other therapeutically bioactive compounds, consisting of one or more pharmaceuticals and/or nutritional supplements of any kind; vi) a formulation of sufficient potency consisting essentially of one or more extracts, combinations and/or derived preparations of bioflavonoids, phytochemicals, preparations and/or anti-oxidants and their various forms, derived in whole or in part, from of any constituent, and of any combination of the plant species of: *Centella asiatica, Curcuma longa, Salix alba, Rosa canina, Hibiscus sabdariffa, Oenothera biennis, Vaccinium myrtillus*, combined in whole or in part, in a formulation consisting of one or more specific trace minerals; and vii) a specific therapeutic formulation comprising one or more plant-derived oils as a lypophilic carrier necessary to facilitate the transport and delivery of the active ingredients in the human body.

In one embodiment, the composition and method can be considered a novel combinatorial treatment for the symptoms of recurring peripheral neuropathy. The composition provides a combination of ingredients that can be used in various methods for decreasing the severity of symptoms associated with of one or more types of peripheral neuropathy and retinopathy in humans, and for specifically modulating the pain and discomfort associated with diabetic peripheral neuropathy in humans, as well as other types of peripheral neuropathy related to the effects of treating cancer patients with various antineoplastic agencies, and peripheral neuropathy related to the effects of treating HIV-AIDs patients with various antiviral regimens.

Advantages of the present invention include, without limitation, convenience, efficacy, safety, fewer adverse events and easier compliance by patients. The combined ingredients in the compositions and extracts of the present invention are particularly useful as stand-alone therapy for treating the pain and discomfort symptoms associated with one or more types of peripheral neuropathy.

In an embodiment of the invention, the composition is to be administered in a therapeutically effective amount with one or more medicinal agents useful for treating diabetes. These medicinal agents can be administered separate from the botanical composition or can be combined with it. In a preferred embodiment, the composition would be administered with anti-diabetes agents in any form, dosage or routing selected from the group consisting of various types of insulin, potentiaters of various types of insulin, and multiple classes of oral anti-diabetic agents approved for use, or will be approved for use, by the Food and Drug Administration (FDA) and/or other national and/or regional medicine regulatory agencies. The methods of administration, dose and routing of the present invention provide for the use of material or ingredient from, or botanical preparation comprising such plant-based ingredients which are in the form of extracts or parts from raw plant materials and/or from an aqueous solution that includes but is not limited to water and alcohol. Such compositions can be in an ingestible form, such as, but not limited to, powders, capsules, liquids, tablets and suspensions.

The combined ingredients in the compositions or extracts of the present invention are particularly useful as stand-alone therapy for treating the pain and discomfort symptoms associated with one or more types of peripheral neuropathy. The composition can be administered in a therapeutically effective amount with one or more medicinal agents useful for treating neuropathic pain of any type. More preferably, the composition may be administered in combination with, prior to, concomitantly with, or after the administration of agents designed to treat neuropathy in any form, dosage or routing selected from the group consisting of various types of pain receptor mediators, including but not limited to multiple classes of oral and intravenous therapeutic and medicinal agents approved for use, or will be approved for use, by the Food and Drug Administration (FDA) and/or other national and/or regional medicine regulatory agencies. The methods of administration, dose and routing of the present invention provide for the use of material or ingredient from, or botanical preparation comprising such plant-based ingredients which are in the form of a granulated extract from raw plant materials and/or from an aqueous solution that includes but is not limited to water and alcohol. Such compositions can be in an ingestible form, such as, but not limited to powders, capsules, liquids, softgels, tablets and suspensions.

The present invention also provides methods of treating diseases and symptoms of diseases in subjects (particularly humans) in need of such treatment which includes administering a therapeutically effective amount of a composition comprising a pharmaceutically acceptable carrier; material or chemical from, and/or botanical preparation and/or combination comprising any part or constituent of the plant species of a plurality of and preferably each of the following botanicals: *Centella asiatica, Curcuma longa, Salix alba, Rosa canina, Hibiscus sabdariffa, Oenothera biennis*, and *Vaccinium myrtillus*. This composition may also include in combination one or more other therapeutically bioactive compounds, including but not limited to vitamins, vitamin-derivatives, plant-derived oils, minerals, medications of any kind and other similar ingredients.

The invention comprises administration of a methodology and composition containing therapeutically effective amounts of ingredients including plant materials, phytochemicals or extracts of seven plant species *Centella asiatica, Curcuma longa, Salix alba, Rosa canina, Hibiscus sabdariffa, Oenothera biennis*, and *Vaccinium myrtillus* alone or in combination with therapeutically effective amounts of various micronutrients and synthetic chemical compounds. The method and composition can be used to modulate specific biological responses, including specific cytokines, chemokines, detoxifying enzymes and gene expression of selected genes, notably consisting of interleukin-1β, interleukin-6, quinone reductase 1 (QR-1) and other phase II detoxifying enzymes, and Gpx3 and Gstp1 among other genes.

The combination of ingredients that includes botanical extracts, alone or in combination with micro-nutrients and synthetic chemical ingredients, is useful as a biological response modifier (a substance that stimulates the body's response to disease) that can be used in various methods to modulate the discomfort and pain of various peripheral neuropathies, including those related to diabetes mellitus, the peripheral neuropathies associated with side effects of various cancer chemotherapies and anti-viral treatments for HIV-AIDS. The compositions can be used to improve the quality of life for diabetic, chemotherapy and HIV-AIDs patients. Treatment compounds and methods encompassed by this invention include, but are not limited to, those useful for treating recurring peripheral neuropathies related to diabetes mellitus as well as recurring peripheral neuropathies related to the side effects of various cancer chemotherapy and peripheral neuropathies related to the side effects of anti-viral treatment for HIV-AIDs. Other treatment compounds and methods encompassed by this invention include those that are useful for treating and/or slowing disease and/or symptom progression specifically related to diabetes-related retinopathy and age and/or disease related wet or dry macular degeneration and related conditions. The compositions and methods can be used for regulating specific cytokines and chemokines, and gene expression of genes thought to be related to the diseases and symptoms mentioned above, specifically modulating specific biological responses, including specific target cytokines, chemokines, detoxifying enzymes and gene expression of selected genes, notably consisting of interleukin-1 beta, interleukin-6, quinone reductase 1 (QR-1) and other phase II detoxifying enzymes, and Gpx3 and Gstp1 among other genes.

This invention combines botanical ingredients and/or extracts together with one or more synthetic chemical and nutrient ingredients in a pharmaceutically acceptable carrier. There are seven plant species (*Centella asiatica, Curcuma longa, Salix alba, Rosa canina, Hibiscus sabdariffa, Oenothera biennis*, and *Vaccinium myrtillus*) chosen to make a particular formulation, and each is selected for their endogenously active phytochemical attributes. The parts of the various botanicals are chosen so as to obtain one or more of the desirable active phytochemical attributes of that botanical, and include leaves, fruit, bark, and roots that are subsequently combined. Formulating the composition with specific extracts of those same plant parts, and/or with oil extracts of these and other plants, can potentiate activity of the composition. That is, by combining plant parts with said extracts and/or oils has advantages which may include, but is not limited to, increasing the therapeutic index of one or more phytochemical compounds, and enhancing specific biological response modulation activities of one or more of the therapeutic compounds and the formulation as a whole.

The compositions and methods of the present invention will be useful for treating any mammal. However, the compositions and methods of the present invention are particularly useful for treating humans.

The compositions and methods include a pharmaceutically acceptable carrier; plant material and/or phytochemical extracts from a plant species a plurality of or each of the following species of herbs: *Centella asiatica, Curcuma longa, Salix alba, Rosa canina, Hibiscus sabdariffa, Oenothera biennis*, and *Vaccinium myrtillus* chosen so as to obtain one or more of the desirable active phytochemical attributes of that botanical, and include leaves, fruit, bark, and roots that may be combined in specific ratios or by a method of processing with specific extracts of those same plant parts, and possibly with oil extracts of those same or other plants, and may be further combined with specific synthetic chemical nutrients. Preferably, combining plant parts with said extracts and/or oils leads to a method of processing and composition that includes, but is not limited to, increasing the therapeutic index of one or more phytochemical compounds, enhancing specific biological activities of one or more of therapeutic compounds and the formulation as a whole. Preferably, the composition comprises a pharmaceutically acceptable carrier, an herbal preparation of *Centella asiatica, Curcuma longa, Salix alba, Rosa canina, Hibiscus sabdariffa, Oenothera biennis*, and *Vaccinium myrtillus*, and a formulation comprising one or more phytochemical extract ingredients. More preferably, the herbal preparation comprises materials, extracts and/or phytochemicals, in various ratios, from *Centella asiatica, Curcuma longa, Salix alba, Rosa canina, Hibiscus sabdariffa, Oenothera biennis*, and *Vaccinium myrtillus* together with carrier oils. Most preferably, this invention comprises materials, extracts and/or phytochemicals, in various ratios, which include and/or are derived from *Centella asiatica, Curcuma longa, Salix alba, Rosa canina, Hibiscus sabdariffa, Oenothera biennis*, and *Vaccinium myrtillus* chosen to make a particular formulation, each selected for their endogenously active phytochemical attributes whereby the parts of the various botanicals are chosen so as to obtain one or more of the desirable active phytochemical attributes of that botanical, and include leaves, fruit, bark, and roots that are combined in specific ratios in a method of processing with specific extracts of the those same plant parts, and with oil extracts of other plants, and various synthetic compounds wherein such attributes of combining plant parts with said extracts are a method of processing that include, but are not limited to, increasing the therapeutic index of one or more phytochemical compounds, enhancing specific biological activities of one or more therapeutic compounds and the formulation as a whole.

The orally administered embodiments of the herbal composition of this invention may be in any convenient form such as, soft gel tablets, suspensions in water, alcohol and/or other non-aqueous media. Most preferably, the orally administered embodiment of the composition is in the form of a soft gel or capsule. A unit dosage may comprise a therapeutically effective amount of the botanical composition, with or without one or more additional agents, for a single daily administration (e.g., orally), or it can be formulated into smaller quantities of each ingredient to provide for multiple doses in a day. A unit dosage will depend upon many factors including age, size, and condition of the individual being treated and the number of times the unit will be taken in a single day. In any event, the entire daily dosage will be that which is physiologically acceptable to an individual and may be administered daily over a prolonged period of time. In the present invention, the formulation is preferably orally administered per day, with part of the total dose preferably taken at two or more different times during the day.

In an embodiment of the invention, compositions of the present invention may be prepared from extracts obtained from a blend or a derivative of the blend of the preferred botanical products used in the invention, comprising materials, plant parts, extracts and/or phytochemicals, in various ratios, which include and/or are derived from 2, 3, 4, 5, 6, or 7 of the following species *Centella asiatica, Curcuma longa, Salix alba, Rosa canina, Hibiscus sabdariffa, Oenothera biennis*, and *Vaccinium myrtillus*. The process of matching specific plant parts (roots, leaves, bark, fruit, essential oils, shoots, flowers or other) with specific matched extracts or oils of one or more desired active ingredients provided by a standardized extract or oil of the same botanical species for the composition of species in the present invention is novel to the present invention (e.g., an exemplary composition might include Evening Primrose material (e.g., leaf) together with Evening Primrose oil, Bilberry material (e.g., leaf), and other ingredients including other plant materials, phytochemicals, extracts, and oils, antioxidants, benfotiamine, taurine, lipoic acid, etc. By combining plant parts (roots, leaves, bark, fruit, essential oils, shoots, flowers or other) from each specific species in a specific matched combination with a pre-selected level of one or more desired active ingredients provided by a standardized extract and/or oil of the same botanical species, the composition can be designed to assure a minimum level of potency necessary to achieve the desired therapeutic effects. By combining plant parts (roots, leaves, bark, fruit, essential oils, shoots, flowers or other) from each specific species in a specific matched combination with a pre-selected level of one or more desired active ingredients provided by a standardized extract or oil of the same botanical species, the composition can further be able to leverage the innate synergistic potentiators only found in minute quantities in each of the plants.

In a preferred embodiment, one method of preparing such a composition of the invention is to extract the active agents from each botanical raw material using an organic solvent typically using an alcohol or hexane extraction, or using a supercritical carbon dioxide extraction. Lipidic extracts and saponifiable extracts can also be used. Further concentration of the active agents can be effected by extracting them from organic solvents back into aqueous solvents at basic pH. In one preferred embodiment involving each botanical raw material, the method comprises the steps: (a) contacting the fruit, seed, plant, bark or root of a species of plant with a polar organic solvent for a time sufficient to form an extract solution, (b) removing particulate matter from the extract solution; (c) isolating the extract solution and removing the polar organic solvent to form a concentrated primary extract, (d) washing the concentrated primary extract with a solvent in which impurities are soluble and the agent is poorly soluble; (e) removing the solvent; and (f) dissolving the desired methylation modifying agent in a polar organic solvent or in water at neutral to basic pH, and (g) combining the first active agent extract of an active ingredient together with other similarly extracted active agents from the other botanical raw ingredients used in the composition.

In some embodiments of the invention, the active botanical materials are further processed and an active extract may be obtained from the botanical materials by contacting the preferred embodiments with a polar solvent e.g., a lower alcohol such as ethanol, or ethyl acetate, for a time sufficient to form an extract solution from the raw material, and then removing at least a portion of the polar solvent from the solution, thus forming a concentrated primary extract. Substantially all of the polar solvent is typically removed. The concentrated primary extract may be used as the active botanical extract.

In another embodiment of the invention, the active botanical ingredients are further processed, purified and are extracted into an alcohol tincture suitable for human consumption.

The present invention provides a method for producing a complex, combinatorial compound (composition) made from various botanical raw materials and their matched extracts and other non-botanical nutrients n that can be well-suited for use in clinical studies under a treatment protocol and more importantly for use in treatment of patients. The method insures that the compound (composition) will be of consistent quality, have consistent therapeutic effects among those age and gender-matched patients with similar disease condition profiles, and most importantly, achieve a standard of potency and quality to be suitable for use in human and mammals a medicinally therapeutic compound (composition).

The present invention provides the ability to control, within an acceptable range of performance, the quality, potency and therapeutic effectiveness of the composition comprised of raw botanical materials, botanical extracts and any other ingredients whether active incipients or excipients. The processed material may include a plurality of active components which exhibit a given biological activity and plurality of inactive components which do not directly exhibit any biological activity of interest.

Some examples of the active phytochemicals in the composition include catechin, gallocatechin, anthocyanidins, anthocyanins, ascorbic acid, campesterol, curcuminoids, ferulic acid, isoquercitrin, isoquercitroside, kaempferide, kaempferitrin, kaempferol-7-glucoside, magnesium, quercetagetin, quercetin-3-o-beta-d-glucoside, quercetin-3-o-galactoside, salicylates, salicylic-acid, and selenium. According to reference databases provided by the United States Department of Agriculture (USDA), Agricultural Research Service, each of the botanicals and plant parts (leaf, root, bark, fruit, etc.) used in the composition of the invention has a myriad of phytochemicals; each of the plant parts has dozens if not hundreds of known active phytochemicals in various isoforms and concentrations; and each species is known for one or more distinct chemical or medicinal activities.

| Botanical Species | Active Phytochemicals (#) Identified in Species | Distinct Chemical Activities (#) for Species |
|---|---|---|
| Centella asiatica | >300 | >580 |
| Curcuma longa | >250 | >650 |
| Salix alba | >120 | >500 |
| Rosa canina | >200 | >560 |
| Hibiscus sabdariffa | >230 | >620 |
| Oenothera biennis | >120 | >520 |
| Vaccinium myrtillus | >300 | >760 |

As an example of phytochemicals for botanicals for use in the composition, it is well-known that *Centella Asiatica* contains several bioactive ingredients, including asiaticoside, brahmoside, madecassoside, thiamine, riboflavin, pyridozine, vitamin K, asparate, glutamate, serine, threonine, alaine, lysine, histidine, magnesioum, calcium and sodium. Thus, either or both or all of the plant material, phytochemicals and extracts derived from the plant materials can be used in the composition of the invention.

Aspects of the present invention are based on the recognition that an active botanical and botanical extract, in synergistic combinations with each other, and in synergistic combinations with other active constituents or nutrients, stimulates an immune system and cellular signaling response that reduces or even prevents oxidant mediated damage and provides beneficial therapeutic effects vis-a-vis reducing the pain and discomfort of peripheral neuropathies of various etiologies, as well as reducing symptoms and disease progression of retinopathy and/or macular degeneration.

Embodiments of the invention provide compositions and methods for reducing or even preventing oxidant mediated damage and providing beneficial therapeutic effects comprising a novel synergistic set of botanical raw materials, in combination with active botanical extracts of the same botanical raw materials, and, in combinations with specific nutrients, wherein the compositions simultaneously induce or inhibit the activities specific genes, up- and/or down regulation the production of specific protein enzymes. These embodiments also include methods of making and using the compositions.

The active botanicals, botanical extracts, synthetic molecules and other nutrient materials of the invention can be combined with ordinary foods to enhance the value of the palatability of the composition. For example, the compositions can be mixed with drinks, food supplements, snacks, bars, and virtually any other food, nutritional product or drink that can be supplemented. Thus, the invention specifically includes food substances of specific types combined with the composition of the invention in specified forms and quantities.

In other embodiments, the compositions of the present invention may be prepared simply by mixing the combination one or more of the active botanicals, specific phytochemicals and/or botanical extracts found in three or more of the five following species of plants: *Centella asiatica, Curcuma Tonga, Salix alba, Rosa canina, Hibiscus sabdariffa, Oenothera biennis,* and *Vaccinium myrtillus* in the present invention together with one or more pharmaceutically acceptable excipients. In this way, the composition can be formulated for administration via several conventionally acceptable routes. The compositions are prepared by mixing the active botanical extracts with one or more inert excipients (e.g., carriers, vehicles, binders, diluents etc.) suitable for the selected route of administration. The term "excipients" as used herein refers to pharmaceutically acceptable organic or inorganic substances which do not deleteriously react with the active compounds. Suitable excipients include, but are not limited to, dietary suitable starch, vegetable oil, vegetable gums, gelatins, soy extracts, sugars, grains, natural and artificial flavorings, and the like. Suitable carriers include, but are not limited to, water, salt solutions, alcohol, plant seed and vegetable oils, glycols, gelatin, lactose, amylose, magnesium stearate, talc, silicic acid, viscous paraffin, perfume oil; fatty acid monoglycerides and diglycerides, fatty acid esters, hydroxymethylcellulose, and the like. The compositions of the invention, including suitable excipients, also may be formulated as syrups and elixirs; additional compositions of the present invention can be readily prepared using technology which is known in the art such as described in detail in Remington's Pharmaceutical Sciences, Twentieth Edition.

More specifically, compositions of the present invention may be in a form suitable for oral use, for example, as tablets, troches, lozenges, pills, aqueous or oily suspensions, solutions, dispersible powders or granules, emulsions, hard or soft capsules, syrups or elixirs, pastes, gels or the like. Compositions intended for oral use may be prepared according to any known method, and such compositions may contain one or more agents selected from the group consisting of sweetening agents, flavoring agents, coloring agents, and preserving agents in order to provide commercially viable, pharmaceutically elegant and palatable compositions. Tablets may contain the active ingredient(s) in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

The terms "carrier oils", refers to any lipid-based carrier materials, oil and/or aqueous solution, derived from any plant seed sources, suitable for administration of the active compounds in the composition of the invention. Carrier oils useful herein include any such materials known in the art that are nontoxic, have stand alone beneficial and therapeutic effects, and do not interact with other components. The term "a pharmaceutically acceptable carrier" refers to any substantially non-toxic carrier conventionally useable for administration in which the active composition of the invention and its derivatives will remain stable and bioavailable.

Compositions of the present invention may be formulated as oily suspensions in a pharmaceutically acceptable carrier such as a soft gelatin capsule whereby the active ingredient(s) is (are) mixed with an aqueous solution or oil medium, including suspending the active ingredient in a plant seed derived or vegetable oil, for example hemp seed oil, evening primrose seed oil, borage seed oil, olive oil, sesame oil or coconut oil. The oily suspensions may contain a thickening agent or other agent necessary to produce a commercially viable product, such as, beeswax, paraffin, lecithin, or cetyl alcohol. Sweetening and flavoring agents may be added to provide a palatable oral composition. These compositions may be preserved by the addition of an antioxidant such as ascorbic acid.

Compositions of the invention can be sterilized and/or mixed with auxiliary agents and other excipients including but not limited to other carrier oils, preservatives, glycerins, stabilizers, waxes, wetting agents, emulsifiers, suspending agents, lecithin, esters or partial esters, buffers, coloring agents, flavorings and/or aromatic substances and the like which do not deleteriously react with the active compounds.

An increase in the level of exogenous anti-oxidants supplied by the composition of the invention is a method that may bring about an improvement in overall health and well-being of a human and/or mammal, which for example, may be an outcome that retards or slows of the process of peripheral nerve derangements and/or retinopathy and/or macular degeneration in a human and/o mammal, which method comprises administering a therapeutically beneficial amount of a composition of the present invention. Thus, the therapeutic effect of the compositions of the present invention can exert a protective effect on the functioning of peripheral nerves; and minimize, prevent or ameliorate symptoms of peripheral nerve disease or disorders, including those relating to eye, or may have any other beneficial effects.

The composition of the invention, and its derivatives, may also be useful in treating diseases, conditions or disorders where derangements in metabolism and/or endogenous mechanisms in a human or mammal, similar to those derangements that cause peripheral neuropathy appear to play a role as evidenced by an association of a chronic disease, condition or disorder with neurodegenerative symptoms. Such chronic diseases, conditions or disorders may include, for example, neurodegenerative diseases, disorders or conditions, such as Parkinson's disease, neuropsychiatric diseases, Alzheimer's disease, heart disease, arthritis, diabetes and certain cancers. The term "neurodegenerative" as used herein refers to a disease, condition or disorder marked by the loss or diminution of an original nerve cell function and functional diseases, conditions or disorders of the nervous system.

Compositions of the present invention, alone or in combination with other active ingredients, may be administered to a subject in a single dose or multiple doses over a period of time, generally by oral administration. As used herein, the term "therapeutically effective amount," refers to the amount of the composition of the invention that result in a therapeutic or overall health and beneficial effect, including a subject's perception of health or general well-being, following its administration to a subject.

The concentration of the active ingredients, including raw plant materials, botanical extracts, carrier oils, and nutrients is preferably selected so as to optimize the composition's therapeutic effects, but is preferably low enough to avoid any safety issues and/or side effects within the scope and sound judgment of the skilled artisan. The effective amount of the composition may vary with the age and physical condition of the patient being treated, the type and severity of the underlying disease(s), the duration and nature of the underlying disease(s), concomitant health condition(s) and concurrent treatment(s), the specific extract, composition or other active ingredient employed, the particular carrier utilized, and other similar factors. Those of skill in the art can readily evaluate such factors and based on this information, determine the particular effective concentration of a composition of the present invention to be used for an intended purpose.

Those skilled in the art can readily determine a therapeutically effective amount of the inventive compositions by determining the therapeutically effective unit dose. As used herein, a "unit dose" refers to the amount of the inventive composition required to produce a response of at least 15% of its maximal effect. The unit dose can be assessed by extrapolating from dose-response curves derived from in-vitro and in-vivo animal model systems, and in human clinical trials. The amount of compounds in the compositions of the present invention which will be effective in the treatment of a particular disorder or condition will depend on the nature of the disorder or condition, and can be determined by standard clinical techniques. The precise amount to be employed in the formulation will also depend on the route of administration as well as the seriousness of the disease or disorder, the mass of the patient and should be decided according to the judgment of the practitioner and each patient's circumstances. Various administration patterns will be apparent to those skilled in the art.

The dosage ranges for the compositions of the present invention are those large enough to produce the desired therapeutic outcome. Preferably, the compositions of the present invention are administered one or more times per day on a regular basis. A typical dose administered to a human is between about 500 mg and about 5 g, preferably between 750 mg and 2 g of the combination of the raw plant materials, active botanical extracts, carrier oils, and nutrients.

Those skilled in the art will recognize that initial indications of the appropriate beneficial amounts (e.g., therapeutic amounts) of the compositions of the invention can be determined in in-vitro and in-vivo animal model systems, and in human clinical trials. One of skill in the art would know to use in vitro studies and human experience to identify a dosage that can safely be administered without generating toxicity or other side effects. For acute treatment where it is desirable to substantially decrease the free-radical and oxidative stress linked to peripheral neuropathy and related symptoms, it is preferred that the beneficial dosage be close to the maximum tolerated dose. For chronic preventive use, lower dosages may be desirable because of concerns about long term effects. However, the individual active botanical extracts, oil carriers, nutrients of the present invention, are commonly believed to be safe and have a history of human use. The compositions may be taken or administered one or more times per day.

While the foregoing written description of the invention will enable one of ordinary skill to make and use several embodiments of the invention, those of ordinary skill will understand and appreciate the existence of variations, combinations, and equivalents of the specific embodiments, method, and examples herein. The invention should therefore not be limited by the above described embodiment, method, and examples, but by all embodiments and methods within the scope and spirit of the invention.

Experiments have been conducted using an exemplary composition which included the following major constituents: Evening Primrose leaf (*oneothera biennis*), Evening Primrose oil, Bilberry leaf (*vaccinium myrtillus*), Bilberry fruit extract, n-acetylcysteine (NAC), and benfotiamine. The exemplary composition included at least one additional botanical material from the group described above, as well as various excipients (e.g., beeswax), oils, and minerals. Experimental results with the exemplary composition demonstrated the efficacy of matching a plant material with an extract or oil of the same plan; the efficacy of using at least 3, and more preferably 4-7 botanicals from the group discussed above; and the efficacy of using antioxidants and other agents in combination with a plurality (two or more) of botanicals.

Based on research performed in one set of in-vitro models using Hepa 1c1c7 murine hepatoma cells, a composition containing the active botanicals, botanical extracts and other nutrients dramatically activated critical Phase II detoxifying enzymes, such as GST, glutathione peroxidase, and glutathione reductase, without an accompanying induction of Phase I enzymes (cytochromes P450 and other monooxygenases) which introduce an oxygen atom in organic substrates but also can metabolically activate relatively innocuous species, such as the conversion of acetonitrile to $HOCH_2CN$.

Without intending to be bound by theory, reactive oxygen species (ROS, e.g., oxygen ions, peroxides) form as a normal byproduct of oxygen metabolism. These species, as well as RNS, can significantly stress a biological system, however, if they are not readily detoxified. Oxidative stress can play a role in a number of human diseases, including atherosclerosis, heart disease, diabetes, Alzheimer's, Parkinson's disease, and cancer. In the face of this significant and ever-present danger, it is not surprising that organisms have developed a complex defense system to deal with oxidative stress. Xenobiotic metabolizing enzymes are an important part of this defense. Phase I enzymes (cytochromes P450 and other monooxygenases) introduce an oxygen atom in organic substrates, but these enzymes can also activate relatively innocuous species, such as the conversion of acetonitrile to $HOCH_2CN$. Phase II enzymes, such as NAD(P)H:quinone oxidoreductase (QR1, NQO1) and glutathione S-transferase (GST), on the other hand, detoxify a number of ROS and other potential toxins. These enzymes may be induced by the xenobiotic responsive element (XRE) along with phase I enzymes, or through activation of the antioxidant responsive element (ARE) without accompanying induction of phase I enzymes. Inducers which act through the XRE are said to be bifunctional; those activating ARE are monofunctional.

Experiments with the exemplary composition containing the active botanicals, botanical extracts and other nutrients did not induce any Phase I enzymes, but did significantly activate Phase II enzymes, notably glutathione S-transferase (GST) and quinone oxidoreductase (QR1), among others.

Experiments with the exemplary composition containing the active botanicals, botanical extracts and other nutrients was found to be monofunctional. A QR1 assay in mutant Hepa cells was used to determine whether induction is monofunctional or bifunctional. Taoc1 and BPrc1 mutant cells are defective in a functional Ah receptor or unable to translocate the receptor-ligand complex to the nucleus, respectively. Induction of QR1 seen in these two cell lines indicates that the sample does not work through the XRE pathway. RT-PCR arrays performed on RNA isolated from cells dosed with the composition provided a fuller picture of the effects the sample has on a variety of drug metabolizing enzymes, and also served to confirm the results of other experiments by quantifying expression of ARE and XRE-inducible genes. Xanthine oxidase catalyzes the production of uric acid, nitric oxide, and other ROS. Its inhibition reduces serum levels of these species, decreasing oxidative stress.

Several other assays were performed in order to evaluate the antioxidant properties of the inventive compositions. These include assays for activity of superoxide dismutases, which catalyze the breakdown of superoxide into oxygen and hydrogen peroxide, and catalase, which aids the decomposition of $H_2O_2$ to water and oxygen, as well as assays measuring hydroxyl radical antioxidant capacity, oxygen radical antioxidant capacity, and total antioxidant capacity. QR1 is a flavoprotein which catalyzes two- or four-electron reduction of a wide variety of quinones, quinone imines, and other nitrogenous compounds. This enzyme has been demonstrated to reduce oxidative stress, particularly in the context of chemoprevention of carcinogenesis. Humans with the homozygous null genotype of the NQO1 gene are characterized by a two-fold increase in the incidence of stomach cancer, as well as increased risk of cutaneous basal cell carcinoma, colon cancer, esophageal squamous cell carcinoma, and lung and urothelial tumors. An inventive composition as described above was found to induce QR1 in Hepa1c1c7 murine hepatoma cells with a CD (concentration required to double activity) value of 39.18±4.4 µg/ml. This activity indicates that the inventive compositions reduce oxidative stress through activation of Phase II detoxifying enzymes. A number of additional assays were chosen to further investigate the invention's activity, including specific assays to determine the extent to which these Phase II enzymes are induced by the composition. GSTs exhibit broad substrate specificity, metabolizing many endogenous and exogenous electrophilic species by conjugating them with glutathione. In addition, some GST-a's exhibit glutathione peroxidase activity. Glutathione peroxidases reduce hydrogen peroxide and lipoperoxides with glutathione serving as a hydrogen donor. Glutathione reductase regenerates oxidized glutathione. Study results with a composition according to the present invention further indicated that the composition increases production of genes regulated by ARE, acting to increase antioxidant activity and reduce oxidative stress.

In another in-vitro model, in a separate study, human retinal pigment epithelial (RPE) cells were plated into 24-well plates at a density of 1×105 cells per well. After 24 hr incubation, the medium was withdrawn, cells were washed and fresh culture medium with $H_2O_2$ (100 µM) was added to the culture with or without the composition at different concentrations. Cells cultured without $H_2O_2$ and the composition were used as the controls. After 24 hr, the conditioned culture medium was collected and centrifuged. Supernatants were stored at −70° C. until analysis. These studies were performed in ARPE and R50 cell lines separately. All groups were tested in triplicate. The amount of various cytokines, chemokines and growth factors protein in the conditioned medium was measured by using the Luminex equipment and Invitrogen Cytokine Human 30-Plex Panel (LHC6003). A 30-plex kit can provide a series of combined reagents for the simultaneous measurement of human IL-1β, IL-1RA, IL-2, IL-2R, IL-4, IL-5, IL-6, IL-7, IL-8, IL-10, IL-12 (p40/p70), IL-13, IL-15, IL-17, TNF-α, IFN-α, IFN-γ, GM-CSF, MIP-1a, MIP-1β, IP-10, MIG, Eotaxin, RANTES, MCP-1, VEGF, G-CSF, EGF, FGF-basic, and HGF.

Initial study results on the effects of the exemplary composition on hydrogen peroxide ($H_2O_2$)-induced expression of various cytokines in human retinal pigment epithelial (RPE) cells demonstrated the following:

1. $H_2O_2$-induced expression of interleukin-1β (IL-1β): IL-1β is a potent pro-inflammatory cytokine. $H_2O_2$ stimulated the expression of IL-1β by RPE in vitro. The botanical composition of the present invention significantly reduced the $H_2O_2$-induced expression of IL-1β in a dose-dependent manner from 0.12 mg/ml (1:3000)-0.7 mg/ml (1:500). Secretion of IL-1β by RPE cells in cells treated with the inventive composition (0.35-0.7 mg/ml) and $H_2O_2$ showed no significant difference as compared with the control (cells not treated with $H_2O_2$), indicating that inventive composition completely blocks the $H_2O_2$-induced expression of IL-1β at these levels.

2. $H_2O_2$-induced expression of interleukin-6 (IL-6): IL-6 is a pro-inflammatory cytokine and is also involved in immune response and the occurrence of autoimmune diseases. $H_2O_2$ stimulated the expression of IL-6 by RPE in vitro. The composition according to the invention significantly reduced the $H_2O_2$-induced expression of IL-6 at a dose-dependent manner from 0.12 mg/ml (1:3000)-0.7 mg/ml (1:500). Secretion of IL-6 by RPE cells in cells treated by the composition (0.7 mg/ml) and $H_2O_2$ showed no significant difference as compared with the control (cells not treated with $H_2O_2$), indicating that the composition completely blocks the $H_2O_2$-induced expression of IL-6 at this level.

3. $H_2O_2$-induced expression of interleukin-10 (IL-10): IL-10 is different from IL-1β and IL-6. IL-1β and IL-6 definitely induce inflammatory response. In general IL-10 inhibits inflammation and immune response but under certain circumstances, IL-10 may have pro-inflammation effect and stimulate the occurrence of auto-immune diseases. Experiments show a composition according to the invention inhibits $H_2O_2$-induced expression of IL-10 by RPE cells.

In-vitro research and assays performed on the exemplary composition, based on models using human RPE cells and Hepa1c1c7 murine hepatoma cells, demonstrated that the composition contained active botanicals, botanical extracts and other nutrients, that can activate specific agonist and antagonist cytokines and induce detoxifying Phase II enzymes, such as GST, glutathione peroxidase, and glutathione reductase, without inducing Phase I enzymes (cytochromes P450 and other monooxygenases) that can potentiate innocuous species into potential toxic species such as the conversion of acetonitrile to $HOCH_2CN$. The in-vitro suite of assays and methods can produce a specific set of benchmark measurements that provides a surrogate measure of production batch/lot quality, potency and therapeutic effect and is a further feature of the invention. These specific benchmark measurements of the total compound provides a qualitative and quantative map of the agonist and antagonist activities of the composition on a specific set of genes that are related to the therapeutic intent and associated with that disease condition.

These specific activity benchmark measurements of total compound performance may be useful to determine if a particular production batch/lot of the compound (composition) as a whole meets the desired levels of therapeutic effect. In this manner, it becomes unnecessary to know the exact amount of any single active component or the potency or biological activity of any marker for any individual botanical material. Preferably, it is total summation of all the individual active components' activities account for the majority of the observed therapeutic effects. As described above, there is a therapeutic correlation between the specific plant species, the selected plant parts, and relevant bioactive phytochemicals. Nevertheless, it is conceivable that isolated individual components of three of the five following species of plants: *Centella asiatica*, *Curcuma longa*, *Salix alba*, *Rosa canina*, *Hibiscus sabdariffa*, *Oenothera biennis*, and *Vaccinium myrtillus*, together with one or more extracts and carrier oils are responsible for 50% of more of the therapeutic activity of the invention.

A novel process and method assures consistent potency of botanical compositions regardless of manufacturing process or type or class of composition. It can include botanical compounds approved by national health regulatory agencies, such as the US FDA, and requiring a prescription from a duly licensed healthcare practitioner or botanical preparations marketed over-the-counter. By applying PCR analysis to assess the botanical composition's impact on the up and down regulation of genes and enzymes in any colony of living cells (animal and/or plant-based), one can use the analytical results to establish a standard measure of potency or activity. This pre-established, scientifically valid measure of potency can be used to assure potency from batch-to-batch or lot-to-lot.

Most, if not all, botanical medicines and their derivatives, contain dozens or even hundreds of active molecules. Moreover, the potency of the same botanical used in medicines can, and does, vary considerably. These variations are typically the result of macro factors such as weather, temperature and moisture and its variations, soil and ground water conditions and its variations and other occurring variations in botanical ecosystems. From crop-to-crop, location-to-location, season-to-season, there may be significant variations in plant characteristics and potency. By applying the analytic results of PCR analysis to assess a botanical composition's impact on the up and down regulation of genes and enzymes in any colony of living cells (animal and/or plant-based), and establishing a baseline signature or fingerprint of activity, one can readily determine any deviation(s) in potency.

This novel process and method is independent of any specific simple, singular, and/or complex botanical composition consisting of any number of ingredients; as well it is independent of any amount or concentration of any botanical composition, including botanical compositions combined with other non-botanical ingredients.

In our laboratory demonstration, murine wild-type Hepa1c1c7 cells were selected and treated with a sample botanical composition at various concentrations. In this instance, for this particular botanical composition, dose-response curves were constructed and, subsequently a concentration of 62 μg/ml of the botanical composition was selected to be tested from among all potential concentrations of the test composition.

In this instance, RT-PCR arrays were performed using RNA isolated from the Hepa 1c1c7 cells treated with the desired concentration botanical composition to give a fuller picture of the effects the sample has on a variety of drug metabolizing enzymes and genes. Total RNA was extracted from the 1c1c7 cells using RT2 qPCR-grade RNA isolation kit, and quantified with UV absorbance. RNA from each group of organs was pooled, and reverse transcription was performed to obtain cDNA via a RT2 First Strand kit. One part appropriately diluted cDNA was added to a master mix partially containing deionized water. This mixture was pipetted into the PCR array, cycled in a Real-time PCR machine using primers for β-actin as an internal control, and Ct values were stated.

As stated, in this instance, a drug metabolism RT-PCR array was employed to analyze the effect of the botanical composition on gene expression. A 'heat' map graphically illustrating the up- and down-regulation of the genes assessed by this array is shown in FIGS. 1 and 2. A number of enzymes and genes were up-regulated following treatment; notably, a number of enzymes and genes, including cytochrome P450 (CYP) genes evaluated in the array were down-regulated or not affected by treatment with the botanical composition.

While the specific array used in the evaluation is primarily designed to assess the expression of gene products related to drug metabolism and potential reduction of oxidative stress, and the tables below illustrate fold change in gene expression in Hepa1c1c7 cells dosed with the botanical composition, the active principle(s) of the novel invention under consideration is not limited to that specific array or assay endpoints; one could use practically any type of array or analytical method and tools, to measure response from one or more genes and/or enzymes.

The invention claimed is:
1. A composition, comprising:
*Oenothera biennis* oil and leaf as a first plant material;
n-acetylcysteine;
R-alpha lipoic acid; and one or more additional plant materials which are different from said first plant material selected from the group consisting of *Centella asiatica, Curcuma longa, Salix alba, Rosa canina, Hibiscus sabdariffa, Camelina sativa* and *Vaccinium myrtillus*, or phytochemicals or extracts or oils derived from said one or more additional plant materials, wherein said composition is an oily suspension or solution formulated for oral dosage.

2. The composition of claim 1 wherein said oily suspension or solution is delivered in a soft gel capsule.

3. The composition of claim 1 wherein said *Oenothera biennis* oil is *Oenothera biennis* seed oil.

4. The composition of claim 1 further comprising thiamine.

5. The composition of claim 1 wherein said one or more additional plant materials includes *Camelina sativa* oil.

6. The composition of claim 1 further comprising quercetin.

7. The composition of claim 1 further comprising one or more agents selected from taurine and benfotiamine.

8. The composition of claim 1 further comprising one or more oils selected from the group consisting of hemp seed oil and sea buckthorn oil.

9. The composition of claim 1 further comprising one or more elements selected from magnesium, zinc, chromium and selenium.

10. The composition of claim 1 further comprising one or more excipients selected from beeswax, lecithin, and glycerin.

11. The composition of claim 1 further comprising biotin.

12. The composition of claim 1 further comprising one or more essential fatty acids.

13. The composition of claim 1 wherein said one or more additional plant materials includes each of *Centella asiatica, Curcuma longa, Salix alba, Rosa canina, Hibiscus sabdariffa, Camelina sativa* and *Vaccinium myrtillus*, or phytochemicals or extracts or oils derived from said one or more additional plant materials.

14. The composition of claim 13 further comprising:
one or more oils selected from the group consisting of hemp seed oil and sea buckthorn oil;
one or more element selected from magnesium, zinc, chromium and selenium;
one or more excipients selected from beeswax, lecithin, and glycerin; and
biotin.

15. An extract of the composition of claim 1.

16. The composition of claim 1 wherein said one or more additional plant materials include at least two of said one or more additional plant materials.

17. The composition of claim 1 wherein said one or more additional plant materials include at least three of said one or more additional plant materials.

18. The composition of claim 1 wherein said one or more additional plant materials includes at least four of said one or more additional plant materials.

19. The composition of claim 1 wherein said one or more additional plant materials includes at least five of said one or more additional plant materials.

20. The composition of claim 1, further comprising:
at least one matched ingredient derived from said one or more additional plant materials, said matched ingredient being selected from phytochemicals or extracts or oils derived from the same plant as said one or more additional plant materials.

* * * * *